United States Patent
Beck

(10) Patent No.: US 8,757,015 B2
(45) Date of Patent: Jun. 24, 2014

(54) METHOD AND DEVICE FOR DETERMINING THE PROPERTIES OF A PRESSURE-MANIPULABLE TEST SAMPLE

(75) Inventor: Uwe Beck, Falkensee (DE)

(73) Assignee: BAM Bundesanstalt fuer Materialforschung und—Pruefung, Berlin (DE)

( * ) Notice: Subject to any disclaimer, the term of this patent is extended or adjusted under 35 U.S.C. 154(b) by 333 days.

(21) Appl. No.: 13/266,018

(22) PCT Filed: Apr. 21, 2010

(86) PCT No.: PCT/EP2010/002614
§ 371 (c)(1),
(2), (4) Date: Nov. 18, 2011

(87) PCT Pub. No.: WO2010/121837
PCT Pub. Date: Oct. 28, 2010

(65) Prior Publication Data
US 2012/0111122 A1    May 10, 2012

(30) Foreign Application Priority Data

Apr. 24, 2009  (DE) .......................... 10 2009 019 303

(51) Int. Cl.
*G01L 1/00*    (2006.01)

(52) U.S. Cl.
USPC ....................................... 73/862.381; 73/783

(58) Field of Classification Search
USPC ....................... 73/760, 783, 862.381, 862.391
See application file for complete search history.

(56) References Cited

U.S. PATENT DOCUMENTS

| | | | | |
|---|---|---|---|---|
| 3,736,501 A | * | 5/1973 | Donkin | 324/242 |
| 4,061,019 A | * | 12/1977 | Blasetti | 73/662 |
| 4,325,910 A | * | 4/1982 | Jordan | 422/64 |
| 4,886,419 A | * | 12/1989 | McCafferty | 416/134 A |
| 6,776,048 B2 | * | 8/2004 | Corrias et al. | 73/819 |
| 6,935,159 B2 | * | 8/2005 | Knight et al. | 73/38 |
| 7,707,895 B2 | | 5/2010 | Beck et al. | |
| 2003/0177840 A1 | * | 9/2003 | Corrias et al. | 73/808 |

FOREIGN PATENT DOCUMENTS

| | | | |
|---|---|---|---|
| JP | 2000131201 A | | 5/2000 |
| JP | 2006343125 A | * | 12/2006 |
| SU | 1439453 A | * | 11/1988 |
| SU | 1478091 A1 | | 5/1989 |
| SU | 1490574 A1 | | 6/1989 |
| WO | 2006050996 A1 | | 5/2006 |

* cited by examiner

*Primary Examiner* — Max Noori
(74) *Attorney, Agent, or Firm* — Dicke, Billig & Czaja, PLLC

(57) ABSTRACT

A method for determining the plasto-elastic properties of a test sample, which can be affected by the action of pressure, includes pressing a test body against a surface of the test sample with a defined force. Plasto-elastic changes of the surface resulting therefrom are recorded during and/or after the pressure application. A centrifugal force generated by rotating the test body around an axis is utilized as a pressure force which is generated by radially movably guiding the test body, which is disposed between the test sample and the axis, relative to the radially fixed test sample.

13 Claims, 2 Drawing Sheets

Figure 1:
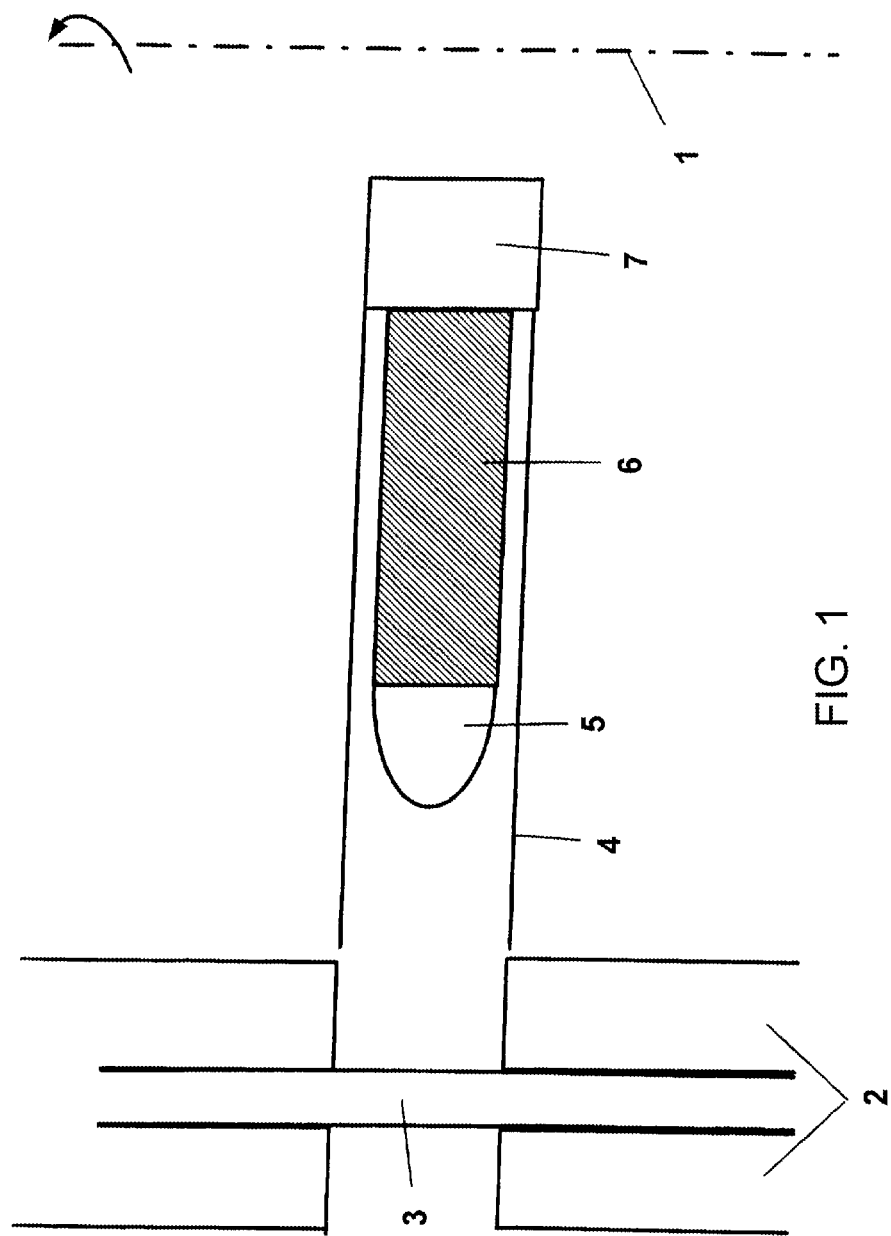

METHOD AND DEVICE FOR DETERMINING THE PROPERTIES OF A PRESSURE-MANIPULABLE TEST SAMPLE

BACKGROUND OF THE INVENTION

Field of the Invention

The invention relates to a method for determining the plasto-elastic properties of a test sample which can be affected by the action of pressure, in which a test body is pressed against a surface of the test sample with a defined force, and the resulting plasto-elastic changes in the surface during and/or after the application of pressure are recorded. The invention also relates to a device for carrying out said method.

In the field of automated materials testing, to determine the plasto-elastic properties under loading by pressure (also known as hardness testing) the only testing techniques which are used around the world at present are ones in which the application of force is achieved by means of mechanical drive systems, e.g. by hydraulic means (large forces) or using e.g. piezo-actuators (small forces).

Of necessity the testing equipment is dimensioned completely differently. In order that the measurement is not corrupted, the test equipment must be able to withstand several times the level of test forces, i.e. it must have an adequate system rigidity.

This test always involves the testing of a sample using a penetrating stamp with a special geometry (e.g. Vickers, Brinell, Knoop, Berkovich, Rockwell, cube vertex, "flat punch" e.g. in the form of a cylinder). Both the sample and the penetrating stamp in the test head must be locked in a fixed position during the test. Two holding devices are therefore necessary (for the sample and the penetrating stamp with the test head). This requires a certain adjustment effort (fixed locking of the sample and the penetrating stamp to the test head and their alignment relative to each other), in particular if multiple samples are to be tested comparatively or with different penetrating stamps (where changing of the test head is necessary).

Both of the holding devices and their fixed mechanical connection must safely withstand the maximum test forces.

At high test forces (hardness testing in the macroscopic range) the absolute test forces necessary (kN to MN) make it essential to over-dimension the testing equipment. For small test forces (hardness testing in the microscopic range) the test forces are, it is true, considerably lower (mN to N), but at the same time considerably higher requirements are made towards the absolute accuracy of the test (μN to mN), which in turn requires over-dimensioning of the test equipment. A force-dependent correction to the measurement relative to the system rigidity is often necessary, wherein force and travel dynamometers are used. This makes the test equipment expensive.

Hardness testing at high or low temperatures or under aggressive environmental conditions (e.g. corrosive gases) is only possible at great expense, because the sample environment would have to be specially screened for the purpose, which due to the holding devices for the sample and test head is not completely possible. If on the other hand the whole test device is exposed to the test atmosphere, it would need to be resistant against it. In each case however the system rigidity varies with temperature. De facto therefore, hardness testing under aggressive environmental conditions is currently not possible.

In the field of breaking strain and tear resistance testing, in particular of films, testing has previously been carried out exclusively using tensile testing machines in which the material to be tested must be clamped on both sides and then the tensile force is successively increased until the material being tested cracks. Typically, such testing machines are equipped with instrumentation and the entire stress-strain diagram is recorded (elastic region, plastic region, flow, fracture).

BRIEF SUMMARY OF THE INVENTION

It is the object of the present invention therefore to specify a method for determining the plasto-elastic properties of a test sample which can be affected by the action of pressure, in which a test body is pressed against a surface of the test sample with a defined force and the resulting plasto-elastic changes in the surface during and/or after the application of pressure are recorded, and a device for carrying out this method which facilitate the testing of a relatively large number of test samples within a short time with low equipment costs, wherein the forces to be applied can be varied within a wide range. Also, different test conditions should be easily produced, for example based on increased or reduced temperatures or an aggressive atmosphere.

This object is achieved according to the invention by a method for determining the plasto-elastic properties of a test sample which can be affected by the action of pressure, in which a test body is pressed against a surface of the test sample with a defined force, and the resulting plasto-elastic changes in the surface during and/or after the application of pressure are recorded. The pressing force is a centrifugal force generated by rotation of the test body about an axis and, in order to apply the pressing force, the test body is guided so that it is radially moveable and disposed in relation to the radially fixed test sample between said sample and the axis. This object is also achieved by a device for carrying out the method, wherein a centrifuge with a drum rotor is provided, on the cylindrical inner wall of which, concentric with the rotational axis, multiple clamping devices are mounted circumferentially distributed and/or above one another in the direction of the rotational axis in order to fix a test sample in such a manner that one of the surfaces thereof is disposed perpendicular to the radial direction. Advantageous extensions of the method and the device arise from the respectively assigned dependent claims.

Because the compressive force is a centrifugal force generated by rotating the test body about an axis, and in order to apply the compressive force the test body is guided so that it is radially moveable and arranged in relation to the radially fixed test sample between this and the axis, the following deficits of previous hardness testing with pressure testing machines can be eliminated:

1. The centrifugal force renders mechanical drive systems for generating the force redundant. This considerably simplifies the test device.
2. With the use of centrifuge technology, a unified test system for small forces (low rotation rates) and large forces (high rotation rates) is available for the first time.
3. With the use of centrifuge technology, a test system is available for the first time which facilitates the simultaneous testing of multiple test samples (also with different penetrating body geometries such as Vickers, Brinell, etc.).
4. With the use of centrifuge technology, only a single and markedly simplified holding device is now required (i.e. that for the test sample). The test body only needs to run in one guide. A fixed mechanical connection between test sample and test body, which must absorb the testing force, can be dispensed with.

5. Load cells are no longer necessary. The testing force is produced only from the rotation speed of the rotor, the distance from the effective centre of mass of the test body to the rotational axis and the mass of the freely moveable test body.

6. In a centrifuge tests at increased or reduced temperatures and in special, e.g. aggressive, environmental conditions are easily realised, since the rotor chamber is an encapsulated system or one that can easily be encapsulated.

7. The rotation rate control of the centrifuge moreover allows almost arbitrary test profiles (rate of force increase or force changes) and programmable test cycles to be implemented in a very simple manner, which is an inestimable advantage, in particular for long-term testing and fatigue testing.

Due to the method according to the invention therefore both the testing process and the test device are considerably simplified. The testing process becomes significantly faster, more reliable and more repeatable, while simultaneously allowing an extended testing range.

The above embodiments relating to hardness testing apply analagously to the testing of breaking strain, tear strength and shear strength (e.g. of films). In contrast to hardness testing, in testing of breaking strain and tear or shear strength, in the region of the guide for the test head the test sample is at least partly unsupported (e.g. by a corresponding hole in the test sample holder).

Instead of being strained up to its yield point in the case of thin films, if the test sample is a sheet made of plastic for example, this can be compressed up to its elastic limit in order to obtain desired information about the material properties.

In hardness testing a (standardised) penetrating stamp (Vickers, Brinell, etc.) is always located on the test head, in testing for breaking strain, tear and shear strength by contrast the test head is fitted with a smooth pressure surface, wherein it is preferably designed e.g. in the form of a cylinder in the case of shear strength, or preferably a hemisphere in the case of breaking strain and tear strength. The test head diameter is to be matched to the diameter of the hole in the test sample holder, so that the test head acting radially from the inside can optimally load the test sample.

With the matching of test head or test stamp mass to the respective task, the test range can also be controlled.

BRIEF DESCRIPTION OF THE SEVERAL
VIEWS OF THE DRAWING

Figure 2:
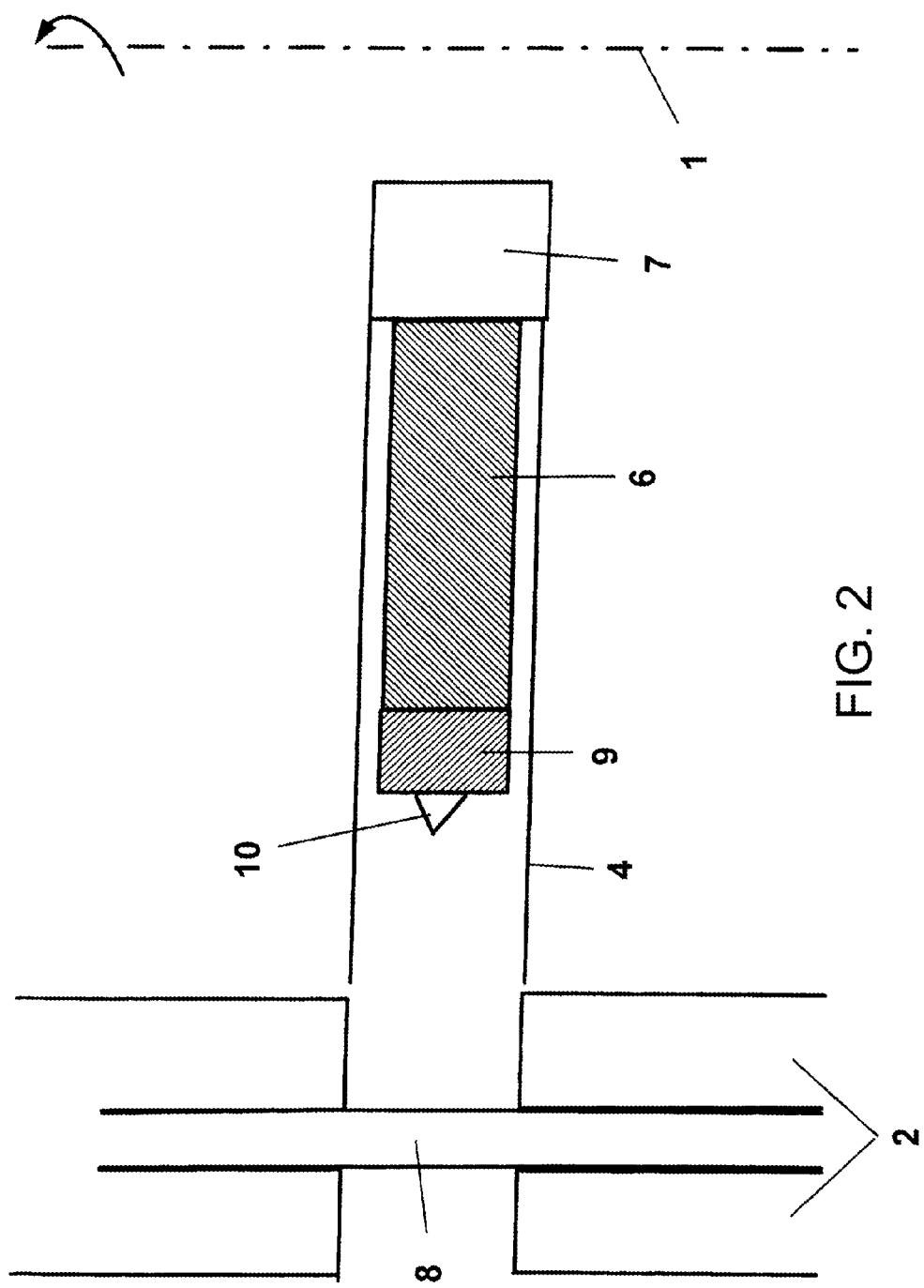

In the following the invention is explained in more detail by means of exemplary embodiments illustrated in the figures. They show:

FIG. 1 a device for testing the breaking strain of a film in a schematic representation, and FIG. 2 a device for testing the hardness of a rigid test sample in a schematic representation.

DESCRIPTION OF THE INVENTION

FIG. 1 shows the rotational axis of a drum rotor, not shown, for example of a bench centrifuge. On the inner wall of the drum rotor a clamping device 2 is fixed with two annular clamping jaws, between which a plastic film 3 is clamped. The clamping is effected around a circular region of the film 3. The film 3 is clamped in such a manner that it extends parallel to the rotational axis 1. On the inner wall of the drum rotor, multiple clamping devices 2 can be fixed next to each other circumferentially as well as above each other. They must be arranged in such a manner that no imbalance occurs during rotation of the drum rotor.

Opposite each clamping device 2 in the unclamped region of the respective test sample, on the side facing towards the rotational axis 1, a sleeve 4 is placed which extends in the radial direction of the drum rotor. The sleeves 4 are fixed inside the drum rotor such that their longitudinal axis extends horizontally. The end of each sleeve 4 pointing towards the associated clamping device 2 is open.

The sleeves 4 are each used for holding a test body which is matched to the inner diameter of the respective sleeve 4 such that it can move freely, but without a large amount of play, in its longitudinal direction. The test body consists of a test head 5, the shape of which is matched to the respective test sample or the type of test. In the present case the breaking strain of the plastic film 3 is to be determined. The surface of the test head 5 facing towards the film is therefore smooth over its entire diameter and has roughly the shape of the shell of a hemisphere. The film 3 can therefore be stretched until it reaches its tearing extension, without it first being cracked by a sharp edge in the test head surface. To determine the shear strength of the film 3 a cylindrical test head is preferably used.

The test body additionally has a cylindrical test stamp 6, which is radially arranged on the inside of the test head 5 and serves to increase the mass of the test body and therefore the centrifugal force, and also to stabilize the guided motion of the test body in the sleeve 4. The test stamp 6 has the same shape for all test samples and all types of test. The material of the test stamp 6 can however be chosen differently, in order to increase the range of the centrifugal forces being generated.

On the end of the sleeve 4 facing the rotational axis 1 a locking device 7 for the test body is located. During the start-up phase of the drum rotor the test body is held by the locking device 7 in its inner position and only released from this after reaching a selectable rotation rate, so that it springs outwards and presses against the film 3. By subsequently increasing the rotation rate of the drum rotor the force acting on the film 3 can be increased up to its tearing point.

It is also possible however to dispense with the locking device. The test body is then held by gravity or friction in its position in the sleeve, and even at low rotation rates moves towards the test sample.

Sensors mounted on the sleeve 4 can detect the respective position of the test body in the sleeve 4. The corresponding signals are wirelessly transmitted to an analysis unit.

The device according to FIG. 2 differs from that of FIG. 1 essentially in that the test sample is not a film but a plate-shaped rigid body 8, the hardness of which is to be measured. The clamping device 2 can be changed so that the remaining free region of the body 8 in FIG. 2 is also supported on the side facing away from the sleeve 4. In addition the test body is fitted with a test head 9, which on the end facing towards the body 8 carries a, for example, conical or pyramid-shaped penetrating body 10. After the release of the test body this penetrates through the locking device 7 into the body 8 and from the penetration depth obtained at a specific rotation rate, the hardness of the body 8 can be determined.

When using a standard commercial bench centrifuge a force range between 0N and a few 10 s of kN can be covered.

The invention claimed is:
1. A method for determining plasto-elastic properties of a test sample which can be affected by an action of pressure, the method comprising the following steps:
radially fixing a rigid test sample;

pressing a test body against a surface of the test sample with a defined centrifugal pressing force generated by rotation of the test body about an axis;

radially moveably guiding the test body, relative to the test sample, between the test sample and the axis, for applying the pressing force;

recording resulting plasto-elastic changes in the surface of the test sample at least one of during or after applying the pressing force;

recording a temporal course of radial motion of the test body while applying the pressing force to the test sample; and recording a penetration depth of the test body in the test sample.

2. The method according to claim 1, which further comprises locking the test body during a start-up phase of the rotation and releasing the test body for radial motion after reaching a pre-defined rotation rate.

3. A method for determining plasto-elastic properties of a test sample which can be affected by an action of pressure, the method comprising the following steps:

radially fixing an elastic test sample in the form of a film by clamping parallel to a rotational axis;

pressing a test body against a surface of the test sample with a defined centrifugal pressing force generated by rotation of the test body about the axis;

radially moveably guiding the test body, relative to the test sample, between the test sample and the axis, for applying the pressing force;

recording resulting plasto-elastic changes in the surface of the test sample at least one of during or after applying the pressing force;

recording a temporal course of radial motion of the test body while applying the pressing force to the test sample; and recording a strain of the test sample caused by applying the pressing force.

4. The method according to claim 3, which further comprises straining the test sample until it reaches a yield point.

5. The method according to claim 3, which further comprises compressing the test sample until it reaches an elastic limit.

6. A device for determining plasto-elastic properties of a test sample which can be affected by an action of pressure, the device comprising:

a centrifuge having a rotational axis, a radial direction and a drum rotor with a cylindrical inner wall surface;

a plurality of clamping devices configured to radially fix a test sample with one surface of the test sample perpendicular to said radial direction;

said clamping devices mounted on said cylindrical inner wall surface concentric with said rotational axis;

said clamping devices being at least one of circumferentially distributed or disposed above one another in direction of said rotational axis;

a test body configured to be pressed against a surface of the test sample with a defined centrifugal pressing force generated by rotation of the test body about said rotational axis;

said test body configured to be radially moveably guided, relative to the test sample, between the test sample and the axis, for applying the pressing force and permitting resulting plasto-elastic changes in the surface of the test sample at least one of during or after applying the pressing force to be recorded.

7. The device according to claim 6, which further comprises sleeves each extending in said radial direction opposite a respective one of said clamping devices on a side of said rotational axis, for radially guiding a respective test body received therein.

8. The device according to claim 7, wherein each of said sleeves has an end opposite a respective one of said clamping devices with a respective locking device for a test body.

9. The device according to claim 4, wherein said clamping devices are configured for clamping at least one of a film or a rigid plate-shaped body.

10. The method according to claim 7, wherein each test body is formed of a radially inner test stamp having the same shape for all test bodies and a radially outer test head for replaceable adaptation to a respective test to be carried out.

11. The device according to claim 10, wherein said test head has a radially outer end carrying an outwardly tapering penetrating body.

12. The device according to claim 11, wherein said penetrating body has a shape selected from the group consisting of pyramid-shaped, conical, spherical and cube vertex-shaped.

13. The device according to claim 10, wherein said test head has a radially outer end with a smooth surface.

* * * * *